United States Patent
Stewart et al.

(10) Patent No.: US 8,835,638 B2
(45) Date of Patent: Sep. 16, 2014

(54) 1,3-OXATHIOLANE DERIVATIVES, PROCESS FOR THE PREPARATION OF 1,3-OXATHIOLANE DERIVATIVES AND INTERMEDIATES THEREOF

(71) Applicant: Apotex Pharmachem Inc., Brantford (CA)

(72) Inventors: Craig Stewart, Mississauga (CA); Michael B. Johansen, Guelph (CA); Probal Kanti Datta, Hamilton (CA); Yajun Zhao, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 13/861,567

(22) Filed: Apr. 12, 2013

(65) Prior Publication Data
US 2013/0274474 A1 Oct. 17, 2013

Related U.S. Application Data

(60) Provisional application No. 61/623,859, filed on Apr. 13, 2012.

(51) Int. Cl.
*C07D 497/20* (2006.01)
*C07D 471/08* (2006.01)

(52) U.S. Cl.
USPC ............................ 546/18; 546/137; 558/252

(58) Field of Classification Search
USPC ...................... 546/18, 137; 558/252
See application file for complete search history.

(56) References Cited

PUBLICATIONS

Nokami et al., Tetrahedron Letters (1995), 36(34), 6099-100.*

* cited by examiner

*Primary Examiner* — Niloofar Rahmani

(57) ABSTRACT

This invention relates to 1,3-oxathiolane derivatives (I), processes for the preparation of 1,3-oxathiolane derivatives and intermediate compounds thereof.

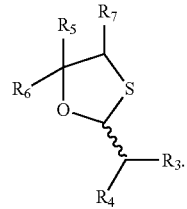

9 Claims, No Drawings

1,3-OXATHIOLANE DERIVATIVES, PROCESS FOR THE PREPARATION OF 1,3-OXATHIOLANE DERIVATIVES AND INTERMEDIATES THEREOF

TECHNICAL FIELD

The invention relates to an improved process for the preparation of 1,3-oxathiolane derivatives and intermediates thereof.

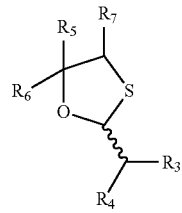

BACKGROUND

The 1,3-oxathiolane ring is a common feature of many useful compounds, including those with medicinal value. Cevimeline is a cholinergic agonist that binds to muscarinic receptors. Muscarinic agonists in sufficient dosage can increase secretion of exocrine glands, such as salivary and sweat glands and increase tone of the smooth muscle in the gastrointestinal and urinary tracts. Cevimeline is marketed in the USA as Evoxac®, and is indicated for the treatment of symptoms of dry mouth in patients with Sjögren's Syndrome. Cevimeline is marketed as the hydrochloride hemihydrate salt with the chemical name cis-2-methylspiro(1,3-oxathiolane-5,3'-quinuclidine) hydrochloride hemihydrate.

U.S. Pat. No. 4,855,290 describes a process for the preparation of 2-methylspiro(1,3-oxathiolane-5,3'-quinuclidine) (1), which comprises the preparation of the epoxide of 3-methylenequinuclidine, which is subsequently reacted with hydrogen sulfide to produce 3-hydroxy-3-mercaptomethylquinuclidine and is condensed with acetaldehyde in the presence of a Lewis acid (e.g. boron trifluoride etherate) to provide 2-methylspiro(1,3-oxathiolane-5,3'-quinuclidine).

U.S. Pat. No. 5,571,918 describes a method for producing 2-methylspiro(1,3-oxathiolane-5,3'-quinuclidine), which comprises reacting 3-hydroxy-3-mercaptomethylquinuclidine or a salt thereof and a carbonyl compound in the presence of a catalyst to produce the cis-form of 2-methylspiro(1,3-oxathiolane-5,3'-quinuclidine) or a salt thereof.

U.S. Pat. No. 4,861,886 describes a method for isomerization of the trans-form of 2-methylspiro(1,3-oxathiolane-5,3'-quinuclidine) or acid addition salts thereof to cis-form 2-methylspiro(1,3-oxathiolane-5,3'-quinuclidine) or acid addition salts thereof in the presence of at least one acid catalyst selected from the group consisting of an organic sulfonic acid, a halide functioning as a Lewis acid, and sulfonic acid.

U.S. Pat. No. 8,080,663 describes a process for the preparation of 2-methylspiro(1,3-oxathiolane-5,3'-quinuclidine) (1), which comprises the preparation of the epoxide of 3-methylenequinuclidine, which is subsequently reacted with thioacetic acid to give the thioacetic acid salt of 3-hydroxy-3-acetoxymercaptomethylquinuclidine, which upon acid or base hydrolysis is converted to 3-hydroxy-3-mercaptomethylquinuclidine, which is subsequently condensed with acetal to provide a mixture of cisitrans 2-methylspiro(1,3-oxathiolane-5,3'-quinuclidine).

WO publication 2011049155 discloses a process for the preparation of a cis-type 2-alkylspiro(1,3-oxathiolane-5,3'-quinuclidine) hydrochloric acid salt, which comprises reacting p-nitrobenzoic acid with a cisitrans isomer mixture of a 2-alkylspiro(1,3-oxathiolane-5,3'-quinuclidine), resolving the resulting product to provide a cis-type 2-alkylspiro(1,3-oxathiolane-5,3') p-nitrobenzoic acid salt, and converting the p-nitrobenzoic acid salt into the hydrochloric acid salt.

SUMMARY

In illustrative embodiments, there is provided a process for the preparation of 1,3-oxathiolane derivatives of Formula I

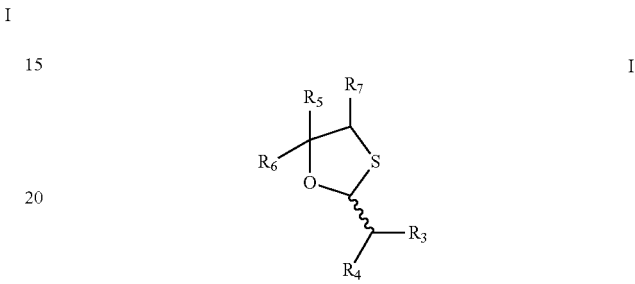

and pharmaceutically acceptable salts thereof comprising cyclizing, in a first solvent and in the presence of a first acid, a compound of Formula VII

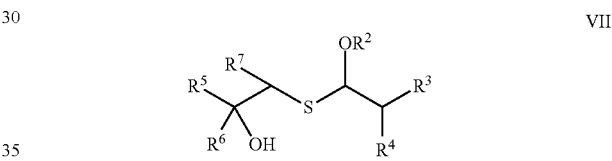

or a salt thereof and optionally adding an acid of a pharmaceutically acceptable salt wherein $R^2$ is alkyl, substituted alkyl, aryl, substituted aryl, or arylalkyl; $R^3$ and $R^4$ are independently hydrogen, alkyl, substituted alkyl, aryl, substituted aryl, or arylalkyl; and either (i) $R^5$, $R^6$ and $R^7$ are independently hydrogen, alkyl, substituted alkyl, aryl, substituted aryl, arylalkyl, or substituted arylalkyl provided that at least one of $R^5$ and $R^6$ is alkyl, substituted alkyl, aryl, substituted aryl, arylalkyl, or substituted arylalkyl; (ii) $R^5$ and $R^6$ form a ring group together with the carbon to which they are bonded and $R^7$ is hydrogen, alkyl, substituted alkyl, aryl, substituted aryl arylalkyl or substituted arylalkyl; or (iii) $R^5$ and $R^7$ form a ring group together with the carbons to which they are bonded and $R^6$ is hydrogen, alkyl, substituted alkyl, aryl, substituted aryl arylalkyl or substituted arylalkyl.

In illustrative embodiments, there is provided a process described herein wherein the compound of Formula VII is a compound of Formula VIIIa

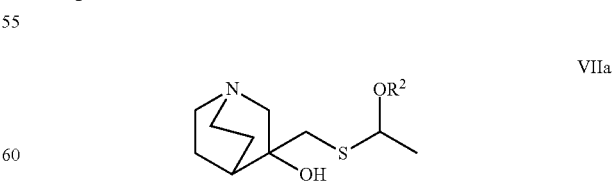

or a salt thereof, wherein $R^2$ is alkyl, substituted alkyl, aryl, substituted aryl, arylalkyl or substituted arylalkyl.

In illustrative embodiments, there is provided a process described herein wherein the compound of Formula VIIIa is a compound of Formula VIIaa

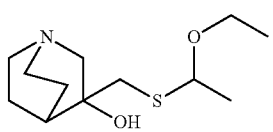

VIIaa or a salt thereof.

In illustrative embodiments, there is provided a process described herein wherein the compound of Formula VIIIa is a compound of Formula VIIab

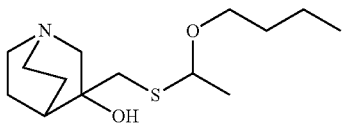

VIIab or a salt thereof.

In illustrative embodiments, there is provided a process described herein wherein the first acid is an organic sulfonic acid, trifluoroacetic acid, a phosphorous oxyacid, sulfuric acid or a Lewis acid.

In illustrative embodiments, there is provided a process described herein wherein the first acid is an organic sulfonic acid or trifluoroacetic acid.

In illustrative embodiments, there is provided a process described herein wherein the first solvent is an aromatic hydrocarbon or an alcohol.

In illustrative embodiments, there is provided a process described herein wherein the compound of Formula VII is prepared by reacting, in the presence of a first base, a compound of Formula VI

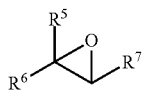

VI with a compound of Formula IV

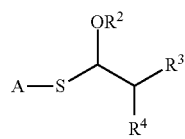

IV or a salt thereof, wherein A is hydrogen or COR$^1$; R$^1$ and R$^2$ are independently alkyl, substituted alkyl, aryl, substituted aryl, or arylalkyl; R$^3$ and R$^4$ are independently hydrogen, alkyl, substituted alkyl, aryl, substituted aryl, or arylalkyl; and either (i) R$^5$, R$^6$ and R$^7$ are independently hydrogen, alkyl, substituted alkyl, aryl, substituted aryl, arylalkyl, or substituted arylalkyl provided that at least one of R$^5$ and R$^6$ is alkyl, substituted alkyl, aryl, substituted aryl, arylalkyl, or substituted arylalkyl; (ii) R$^5$ and R$^6$ form a ring group together with the carbon to which they are bonded and R$^7$ is hydrogen, alkyl, substituted alkyl, aryl, substituted aryl arylalkyl or substituted arylalkyl; or (iii) R$^5$ and R$^7$ form a ring group together with the carbons to which they are bonded and R$^6$ is hydrogen, alkyl, substituted alkyl, aryl, substituted aryl arylalkyl or substituted arylalkyl.

In illustrative embodiments, there is provided a process described herein wherein the compound of Formula VII is not isolated.

In illustrative embodiments, there is provided a process for the preparation of a compound of Formula VII:

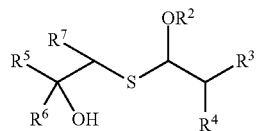

VII comprising reacting, in the presence of a first base, a compound of Formula VI

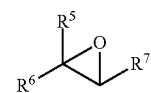

VI with a compound of Formula IV

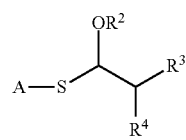

IV or a salt thereof, wherein A is hydrogen or COR$^1$; R$^1$ and R$^2$ are independently alkyl, substituted alkyl, aryl, substituted aryl, or arylalkyl; R$^3$ and R$^4$ are independently hydrogen, alkyl, substituted alkyl, aryl, substituted aryl, or arylalkyl; and (i) R$^5$, R$^6$ and R$^7$ are independently hydrogen, alkyl, substituted alkyl, aryl, substituted aryl, arylalkyl, or substituted arylalkyl provided that at least one of R$^5$ and R$^6$ is alkyl, substituted alkyl, aryl, substituted aryl, arylalkyl, or substituted arylalkyl; (ii) R$^5$ and R$^6$ form a ring group together with the carbon to which they are bonded and R$^7$ is hydrogen, alkyl, substituted alkyl, aryl, substituted aryl arylalkyl or substituted arylalkyl; or (iii) R$^5$ and R$^7$ form a ring group together with the carbons to which they are bonded and R$^6$ is hydrogen, alkyl, substituted alkyl, aryl, substituted aryl arylalkyl or substituted arylalkyl.

In illustrative embodiments, there is provided a process described herein wherein the compound of Formula VII is a compound of Formula VIIIa:

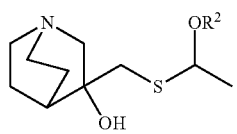

VIIa or a salt thereof wherein R$^2$ is alkyl, substituted alkyl, aryl, substituted aryl, or arylalkyl.

In illustrative embodiments, there is provided a process described herein wherein the compound of Formula VIIIa is a compound of Formula VIIaa

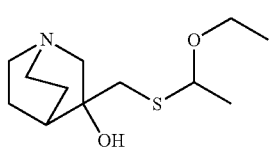

or a salt thereof.

In illustrative embodiments, there is provided a process described herein wherein the compound of Formula VIIIa is a compound of Formula VIIIab

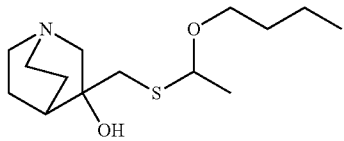

or a salt thereof.

In illustrative embodiments, there is provided a process for the preparation of a compound of Formula VII:

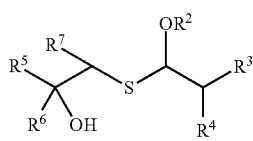

comprising epoxidation of a compound of Formula V

to provide a compound of Formula VI

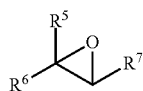

and reacting, in the presence of a first base, the compound of Formula VI with a compound of Formula IV or a salt thereof:

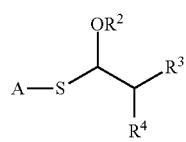

wherein A is hydrogen or $COR^1$; $R^1$ is alkyl, substituted alkyl, aryl, substituted aryl, or arylalkyl; $R^2$ is alkyl, substituted alkyl, aryl, substituted aryl, or arylalkyl; $R^3$ and $R^4$ are independently hydrogen, alkyl, substituted alkyl, aryl, substituted aryl, or arylalkyl; and either (i) $R^5$, $R^6$ and $R^7$ are independently hydrogen, alkyl, substituted alkyl, aryl, substituted aryl, arylalkyl, or substituted arylalkyl provided that at least one of $R^5$ and $R^6$ is alkyl, substituted alkyl, aryl, substituted aryl, arylalkyl, or substituted arylalkyl; (ii) $R^5$ and $R^6$ form a ring group together with the carbon to which they are bonded and $R^7$ is hydrogen, alkyl, substituted alkyl, aryl, substituted aryl arylalkyl or substituted arylalkyl; or (iii) $R^5$ and $R^7$ form a ring group together with the carbons to which they are bonded and $R^6$ is hydrogen, alkyl, substituted alkyl, aryl, substituted aryl arylalkyl or substituted arylalkyl.

In illustrative embodiments, there is provided a process described herein wherein the compound of Formula VII is a compound of Formula VIIIa

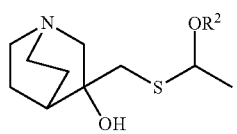

or a salt thereof wherein $R^2$ is alkyl, substituted alkyl, aryl, substituted aryl, or arylalkyl.

In illustrative embodiments, there is provided a process described herein wherein the compound of Formula VIIIa is a compound of Formula VIIaa

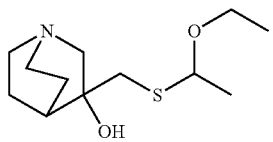

or a salt thereof.

In illustrative embodiments, there is provided a process described herein wherein the compound of Formula VIIIa is a compound of Formula VIIab

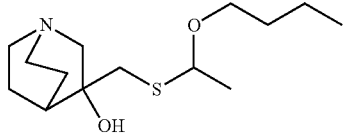

or a salt thereof.

In illustrative embodiments, there is provided a process described herein wherein the compound of Formula IV is acetyl thioethoxyethylacetal.

In illustrative embodiments, there is provided a process described herein wherein the compound of Formula IV is acetyl thiobutoxyethylacetal.

In illustrative embodiments, there is provided a process described herein wherein the epoxidation is conducted in the presence of a sulfur ylide.

In illustrative embodiments, there is provided a process described herein wherein the epoxidation is conducted in the predence of trimethylsulfoxonium iodide and dimethylsulfoxide.

In illustrative embodiments, there is provided a process for the preparation of a compound of Formula IVa:

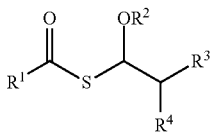

(IVa)

comprising reacting, in the presence of a second acid, a compound of Formula II:

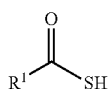

II with a compound of Formula III or IIIa:

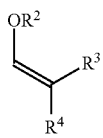

III

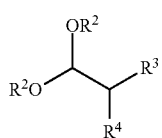

IIIa wherein $R^1$ is alkyl, substituted alkyl, aryl, substituted aryl, or arylalkyl; $R^2$ is alkyl, substituted alkyl, aryl, substituted aryl, or arylalkyl; $R^3$ and $R^4$ are independently hydrogen, alkyl, substituted alkyl, aryl, substituted aryl, or arylalkyl.

In illustrative embodiments, there is provided a process described herein wherein the second acid is an organic sulfonic acid or a Lewis acid.

In illustrative embodiments, there is provided a process described herein wherein the Lewis acid is $SnCl_4$, $TiCl_4$, $BF_3$, or $OEt_2$ In illustrative embodiments, there is provided a process described herein wherein the second acid is p-toluenesulfonic acid, pyridinium toluenesulfonic acid or camphorsulfonic acid.

In illustrative embodiments, there is provided a process described herein wherein the compound of Formula II is thioacetic acid, and the compound of Formula III is ethyl vinyl ether.

In illustrative embodiments, there is provided a process described herein wherein the compound of Formula II is thioacetic acid, and the compound of Formula III is butyl vinyl ether.

In illustrative embodiments, there is provided a compound of Formula VII

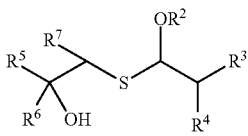

VII or a salt thereof wherein $R^2$ is alkyl, substituted alkyl, aryl, substituted aryl, or arylalkyl; $R^3$ and $R^4$ are independently hydrogen, alkyl, substituted alkyl, aryl, substituted aryl, or arylalkyl; and either (i) $R^5$, $R^6$ and $R^7$ are independently hydrogen, alkyl, substituted alkyl, aryl, substituted aryl, arylalkyl, or substituted arylalkyl provided that at least one of $R^5$ and $R^6$ is alkyl, substituted alkyl, aryl, substituted aryl, arylalkyl, or substituted arylalkyl; (ii) $R^5$ and $R^6$ form a ring group together with the carbon to which they are bonded and $R^7$ is hydrogen, alkyl, substituted alkyl, aryl, substituted aryl arylalkyl or substituted arylalkyl; or (iii) $R^5$ and $R^7$ form a ring group together with the carbons to which they are bonded and $R^6$ is hydrogen, alkyl, substituted alkyl, aryl, substituted aryl arylalkyl or substituted arylalkyl.

In illustrative embodiments, there is provided 3-hydroxy-3-[(1-ethoxyethyl)mercaptomethyl]quinuclidine and acid addition salts thereof.

In illustrative embodiments, there is provided 3-hydroxy-3-[(1-butoxy-1-ethyl)mercaptomethyl]quinuclidine and acid addition salts thereof.

In illustrative embodiments, there is provided 3-hydroxy-3-[(1-ethoxyethyl)mercaptomethyl]quinuclidine.

In illustrative embodiments, there is provided 3-hydroxy-3-[(1-butoxy-1-ethyl)mercaptomethyl]quinuclidine.

In illustrative embodiments, there is provided 3-hydroxy-3-[(1-ethoxyethyl)mercaptomethyl]quinuclidine benzoic acid salt.

DETAILED DESCRIPTION

As used herein, the term "substituted" refers to the replacement of a hydrogen atom on a compound with a substituent group. A substituent may be a non hydrogen atom or multiple atoms of which at least one is a non-hydrogen atom and one or more may or may not be hydrogen atoms. For example, without limitation, substituted compounds may comprise one or more substituents selected from the group consisting of: R'', OR'', NR''R''', SR'', halogen, SiR''R'''R'''', OC(O)R'', C(O)R'', $CO_2R''$, CONR''R''', NR'''C(O)$_2$R'', S(O)R'', S(O)$_2$R'', CN and $NO_2$.

As used herein, each R'', R''', and R'''' may be selected, independently, from the group consisting of: hydrogen, halogen, oxygen, substituted or unsubstituted heteroalkyl, substituted or unsubstituted aryl, substituted or unsubstituted alkyl, alkoxy or thioalkoxy groups, and arylalkyl groups.

As used herein, the term "alkyl" by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (e.g. $C_1$-$C_{10}$ or 1- to 10-membered means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

In some embodiments, the alkyl is ethyl or n-butyl.

The term "lower alkyl" comprises straight chain or branched chain saturated hydrocarbon groups having 1 to 4 carbon atoms, for instance, methyl, ethyl, propyl, isopropyl, butyl, isobutyl, sec-butyl, and t-butyl. Lower alkyls may be substituted or unsubstituted.

In some embodiments, the lower alkyl is ethyl or n-butyl.

The term "short chain alkyl" means an alkyl group having 1 to 3 carbon atoms. Short chain alkyls may be substituted or unsubstituted.

In some embodiments, the short chain alkyl is ethyl

As used herein, the term "aryl" by itself or as part of another substituent, means, unless otherwise stated, a polyunsaturated, aromatic substituent which can be a single ring or multiple rings (often from 1 to 3 rings) which are fused together or linked covalently. As used herein, "Aryl" may be a hydrocarbon or may be a heteroaryl "Heteroaryl" refers to an aryl group that contains from one to four heteroatoms selected from N, O, and S, wherein the nitrogen and sulfur atoms are optionally oxidized, and the nitrogen atom(s) are optionally quaternized. A heteroaryl substituent may be attached to the remainder of the molecule through one or more heteroatoms. Non limiting examples of aryl and heteroaryl groups include, for example, phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, etc.) including those alkyl groups in which a carbon atom containing group (e.g., a methylene group) has been replaced by, for example, an oxygen atom (e.g., phenoxymethyl, 2-pyridyloxymethyl, 3-(1-naphthyloxy)propyl, etc).

As used herein, the term "ring group" means a mono- or poly-carbocyclic or heterocyclic ring which may be fully saturated, mono- or polyunsaturated and may be fused together or linked covalently having from 3 to 11 atoms, excluding hydrogen atoms. Examples include indane, adamantine, quinuclidine, and cyclohexane.

1,3-Oxathiolane derivatives and their intermediate compounds may be prepared according to Scheme 1 starting from a compound of Formula II.

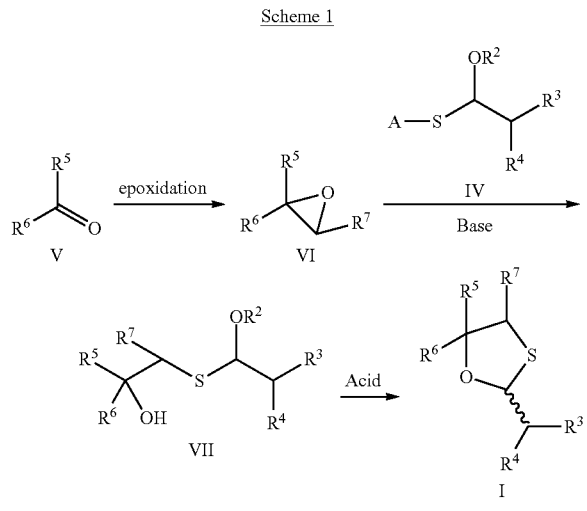

Scheme 1

The first acid may be an organic acid or inorganic acid. The first acid may be selected from the group consisting of organic sulfonic acids (e.g. p-toluenesulfonic acid, camphorsulfonic acid), trifluoroacetic acid, phosphorous oxyacids, sulfuric acid and Lewis acids (e.g. $SnCl_4$, $TiCl_4$, $BF_3.OEt_2$).

In some embodiments, the first acid is p-toluenesulfonic acid.

The reaction of a compound of Formula VII with a first acid may be conducted in a first solvent. The first solvent may be a suitable protic or aprotic organic solvent. The first solvent may be an alcohol such as, for example, methanol, ethanol, propanol, isopropanol or butanol, an alkyl ether such as, for example, tetrahydrofuran, dioxane, diethyl ether, methyl t-butyl ether, diisopropyl ether or butyl ether, an alkyl ester such as, for example, ethyl acetate or isopropyl acetate, a ketone such as, for example, acetone, methyl ethyl ketone or methyl isobutyl ketone, an aromatic or aliphatic hydrocarbon such as, for example, toluene, xylenes, hexanes or heptanes, a nitrile such as, for example, acetonitrile, propionitrile, butyronitrile or benzonitrile, an N,N-dialkylamides such as, for example, N,N-dimethylformamide, N,N-dimethylacetamide or N-methyl-2-pyrrolidinone, a sulfoxide or sulfones, such as,for example, dimethyl sulfoxide or sulfolane, a halogenated hydrocarbon such as, for example, dichloromethane or dichloroethane), or mixtures thereof.

The reaction of a compound of Formula VII with a first acid conducted in a first solvent may be performed at temperatures ranging from about −10° C. to the boiling point of the first solvent, most preferably from about 0° C. to about 80° C.

The reaction of a compound of Formula VIIIa with a first acid conducted in a first solvent may produce a cis/trans mixture of 1,3-oxathiolane derivatives. In some cases, the cis/trans ratio of the product may be from about 1:1 to about 10:1 respectively.

The first base may be any suitable organic or inorganic base. The first base may be selected from metal hydroxides, alkoxides, carbonates, phosphates and amides.

In some embodiments, the first base may be potassium t-butoxide or potassium carbonate.

The reaction of the compound of Formula VI with a compound of Formula IV may be conducted in a second solvent. The second solvent may be any suitable protic or aprotic organic solvent. The second solvent may be the same as or different from the first solvent selected from the group consisting of alcohols (e.g. methanol, ethanol, propanol, isopropanol, butanol), alkyl ether (e.g. tetrahydrofuran, dioxane, diethyl ether, methyl t-butyl ether, diisopropyl ether, butyl ether), alkyl ester (e.g. ethyl acetate, isopropyl acetate), ketones (e.g. acetone, methyl ethyl ketone, methyl isobutyl ketone), aromatic, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

The reaction of a compound of Formula VI with a compound of Formula IV conducted in a second solvent may be performed at temperatures ranging from about −20° C. to about 50° C., often from about 0° C. to about 30° C.

Compounds of Formula VII may be isolated and/or purified by conversion to an organic acid salt, wherein the organic acid is any suitable acid that forms an acid addition salt and does not induce cyclization. The organic acid may be, for example, a carboxylic acid (e.g. benzoic acid, acetic acid, propionic acid, malic acid, benzoic acid, salicylic acid, fumaric acid or the like), an amino acid, or a hydroxyacid.

In some embodiments, the organic acid salt is a benzoate salt.

Optionally, following the reaction of a compound of Formula VI with a compound of Formula IV, compounds of Formula VII may be used directly in the next step without isolation or purification.

Epoxidation of compounds of formula V may be conducted using processes known to those skilled in the art for conversion of carbonyl compounds to the corresponding epoxides (e.g. Corey-Chaykovsky Reaction).

Compounds of formula IVa may be made by reacting compounds of formula II, in the presence of a second acid, with compounds of Formula III or IIIc. The second acid may be an organic acid or inorganic acid. The second acid may be selected from the group consisting of organic sulfonic acids (e.g. p-toluenesulfonic acid, pyridinium toluenesulfonic acid, camphorsulfonic acid) and Lewis acids (e.g. $SnCl_4$, $TiCl_4$, $BF_3.OEt_2$).

The reaction of the compound of Formula II with a compound of Formula III or IIIa may be conducted in a third solvent. The third solvent may be the same as or different from the second solvent.

The reaction of a compound of Formula II with a compound of Formula III or IIIa conducted in a third solvent may be performed at temperatures ranging from about −10° C. to about 30° C., often from about 0° C. to about 10° C.

Optionally, following the reaction of a compound of Formula II with a compound of Formula III or Formula IIIa in the presence of a second acid in a third solvent, a compound of Formula IV may be optionally used in the next step without further purification or isolation of the product.

1,3-Oxathiolane derivatives and the intermediates thereof may be prepared as set out in Schemes 2 and 3. Exemplary reagents and conditions for these reactions are disclosed herein in examples.

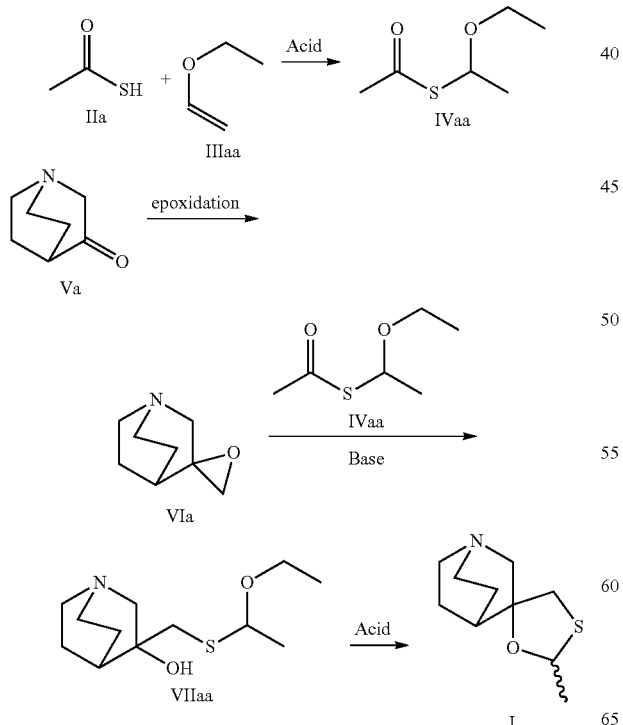

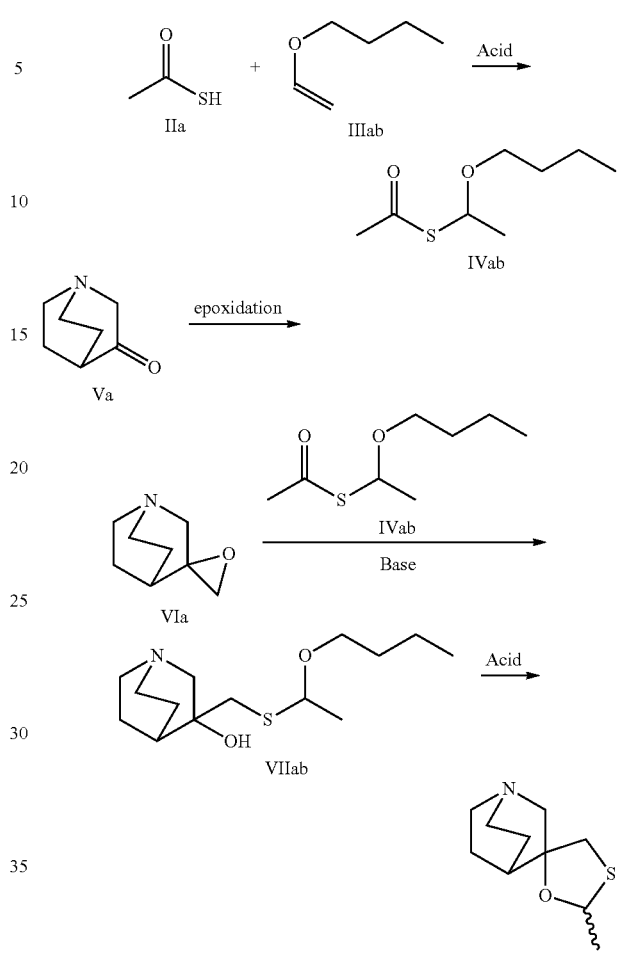

EXAMPLES

The following examples are illustrative of some of the embodiments of the invention described herein. These examples do not limit the spirit or scope of the invention in any way.

Example 1

Preparation of Acetyl Thioethoxyethylacetal

To a solution of thioacetic acid (5.46 g, 71.7 mmol) in dichloromethane (30 mL) was added p-toluenesulfonic acid monohydrate (1.36 g, 7.17 mmol) and the reaction mixture was cooled to 0-5° C. Ethyl vinyl ether (5.43 g, 75.0 mmol) was then slowly added over a period of 20 minutes and the reaction was maintained at 0-5° C. for a further 15 minutes before warming to room temperature for 40 minutes. The reaction mixture was then transferred to a separatory funnel, charged with saturated sodium bicarbonate solution (35 mL) and separated. The aqueous phase was then further extracted with dichloromethane (2×25 mL), the organic extracts were then combined and washed with saturated sodium chloride solution (15 mL). The organic extracts were concentrated to give 12.35 g of a clear colourless oil, constituting of 15:85 by weight of dichloromethane and acetyl thioethoxyethylacetal (10.50 g, 70.9 mmol, 98%) respectively. The product was used in the next step without any further purification.

$^1$H NMR (400 MHz, CDCl$^3$) δ 5.45 (q, J=6.5 Hz, 1H), 3.67-3.59 (m, 1H), 3.50-3.42 (m, 1H), 2.34 (s, 3H), 1.59 (d, J=6.5 Hz, 3H), 1.18 (t, 7.0 Hz, 3H)

Example 2

Preparation of Acetyl Thiobutoxyethylacetal

To a solution of thioacetic acid (6.58 g, 86.4 mmol) in dichloromethane (35 mL) was added p-toluenesulfonic acid monohydrate (1.64 g, 8.64 mmol) and the reaction mixture was cooled to 0-5° C. Butyl vinyl ether (9.28 g, 90.8 mmol) was then slowly added over a period of 15 minutes and the reaction was maintained at 0-5° C. for a further 30 minutes before warming to room temperature for 90 minutes. The reaction mixture was then transferred to a separatory funnel, charged with saturated sodium bicarbonate solution (15 mL) and separated. The aqueous phase was then further extracted with dichloromethane (2×50 mL), the organic extracts were combined and washed with water (20 mL). The organic extracts were then concentrated to give 17.14 g of a clear colourless oil, constituting of 14:86 by weight of dichloromethane and acetyl thiobutoxyethylacetal (14.74 g, 83.6 mmol, 97%) respectively. The product was used in the next step without any further purification.

$^1$H NMR (400 MHz, CDCl$_3$) δ 5.42 (q, J=6.3 Hz, 1H), 3.60-3.54 (m, 1H), 3.42-3.38 (m, 1H), 2.35 (s, 3H), 1.58 (m, 2H), 1.36 (sextet, J=7.4 Hz, 2H), 0.92 (t, J=7.4 Hz, 3H)

Example 3

Preparation of the Epoxide of 3-Methylenequinuclidine

A mixture of the hydrochloride salt of 3-quinicildinone (2, 120 g, 795.7 mmol) and trimethylsulfoxonium iodide (219 g, 993.3 mmol) in dimethylsulfoxide (91.0 g, 0.63 mol) was cooled to 0-5° C. in an ice/water bath under nitrogen atmosphere. A solution of potassium tert-butoxide (201 g, 1789.1 mmol) in dimethylsulfoxide (500 mL) was added dropwise over 45 minutes. The mixture was warmed gradually to room temperature and stirred for an additional 16 hours at room temperature. After cooling to 0-5° C. (ice/water bath) the mixture was poured into an ice/water mixture (500 g) and then sodium chloride (300 g) was added. The mixture was stirred for 30 minutes and extracted with toluene (3×400 mL). The toluene phase was dried over sodium sulfate, filtered and evaporated to furnish the epoxide of 3-methylenequinuclidine (60 g, 431.7 mmol, 54% yield) as a yellow oil. The product could be used in the next step neat or as toluene solution after the extraction without further purification.

$^1$H NMR (400 MHz, CDCl$_3$): δ=3.10 (d, 1H, J=14.6 Hz); 2.98-2.77 (m, 5H); 2.74 (d, 1H, J=4.8 Hz); 2.70 (d, 1H, J=4.8 Hz); 1.96-1.89 (m, 1H); 1.79-1.62 (m, 2H); 1.60-1.54 (m, 1H); 1.38-1.36 (m, 1H).

LRMS (ES+): 140.0 (100, M+H$^+$).

Example 4

Preparation of 3-hydroxy-3-[(1-ethoxyethyl)mercaptomethyl]quinuclidine

To a solution of the epoxide of 3-methylenequinuclidine (13.9 g, 100 mmol) in toluene (60 mL) was added acetyl thioethoxyethylacetal (15.0 g, 101 mmol) and methanol (75 mL). The mixture was cooled to 0-5° C. at which time potassium tert-butoxide (1.13 g, 10.1 mmol) was added in one portion. The reaction mixture was stirred for 30 minutes at which time the ice bath was removed and the reaction mixture was allowed to warm to room temperature for an additional 1 hour. To the reaction mixture was added 10% sodium hydroxide solution (75 mL) followed by toluene (50 mL). The phases were separated and the aqueous phase was extracted with toluene (2×100 mL) followed by removal of solvents to give 3-hydroxy-3-[(1-ethoxyethyl)mercaptomethyl]quinuclidine (20 g, 81.5 mmol, 82%, 1:1 mixture of diastereomers) as a pale yellow oil. The product was used in the next step without any further purification.

$^1$H NMR (400 MHz, CDCl$_3$, 1:1 mixture of diastereomers) δ 4.71 (q, J=6.5 Hz, 0.5H), 4.63 (q, J=6.5 Hz, 0.5H), 3.85-3.78 (m, 0.5H), 3.73-3.63 (m, 0.5H), 3.59-3.40 (m, 2H), 3.10-2.65 (m, 8H), 2.12-2.01 (m, 1H), 1.95-1.89 (m, 1H), 1.65-1.45 (m, 5H), 1.35-1.28 (m, 1H), 1.23-1.18 (m, 3H)

Example 5

Preparation of 3-hydroxy-3-[(1-ethoxyethyl)mercaptomethyl]quinuclidine

To a solution of the epoxide of 3-methylenequinuclidine (9.50 g, 68.3 mmol) in toluene (45 mL) was added acetyl thioethoxyethylacetal (10.22 g, 68.9 mmol), methanol (48 mL), and toluene (48 mL). The mixture was cooled to 0-5° C. at which time potassium carbonate (9.52 g, 68.9 mmol) was added in one portion. The reaction mixture was stirred for 2 hours at which time the ice bath was removed and the reaction mixture was allowed to warm to room temperature. To the reaction mixture was added water (100 mL) followed by toluene (50 mL). The phases were separated and the aqueous phase was extracted with toluene (2×100 mL) followed by removal of solvents to give 3-hydroxy-3-[(1-ethoxyethyl)mercaptomethyl]quinuclidine (15.52 g, 63.3 mmol, 93%, 1:1 mixture of diastereomers) as a pale yellow oil. The product was used in the next step without any further purification.

Example 6

Preparation of 2-[(1-ethoxyethyl)sulfanyl]-1-phenylethanol

To a solution of styrene oxide (2.11 g, 18.5 mmol) and acetyl thiobutoxyethylacetal (2.79 g, 18.8 mmol) in toluene (11 mL) was added methanol (11 mL) and the reaction mixture was cooled to 0-5° C. Potassium tert-butoxide (0.211 g, 1.88 mmol) was then added and the reaction was maintained at 0-5° C. for 30 minutes before warming to room temperature for an additional 24 hours. The reaction mixture was then transferred to a separatory funnel and charged with saturated potassium carbonate solution (20 mL) and toluene (20 mL). The phases were separated and the aqueous phase was extracted with toluene (2×25 mL). The organic extracts were combined and washed with saturated sodium chloride solution (30 mL) and concentrated under reduced pressure to provide a yellow oil. The crude product was purified by column chromatography to give the title product (1.5 g, 6.7 mmol) in 36% yield as a colourless oil.

$^1$H NMR (400 MHz, CDCl$_3$, mixture of diastereomers) δ 7.40-7.31 (m, 4H), 7.29-7.23 (m, 1H), 4.80-4.65 (m, 2H), 3.92-3.78 (m, 1H), 3.70-3.62 (m, 1H), 3.60-3.45 (m, 1H), 3.10-2.95 (m, 1H), 2.85-2.75 (m, 1H), 1.65-1.52 (m, 3H), 1.35-1.20 (m, 3H)

Example 7

Preparation of 2-[(1-ethoxyethyl)sulfanyl]cyclohexanol

To a solution of cyclohexene oxide (1.84 g, 18.7 mmol) and acetyl thiobutoxyethylacetal (2.83 g, 19.1 mmol) in toluene (9 mL) was added methanol (9 mL) and the reaction mixture was cooled to 0-5° C. Potassium tert-butoxide (0.214 g, 1.91 mmol) was then added and the reaction was maintained at 0-5° C. for 30 minutes before warming to room temperature for an additional 24 hours. The reaction mixture was then transferred to a separatory funnel and charged with saturated potassium carbonate solution (20 mL) and toluene (20 mL). The phases were separated and the aqueous phase was extracted with toluene (2×25 mL). The organic extracts were combined and washed with saturated sodium chloride solution (30 mL) and concentrated under reduced pressure to provide a colourless oil. The crude product was purified by column chromatography to give the title product (1.6 g, 7.8 mmol) in 42% yield as a colourless oil.

Example 8

Preparation of 3-hydroxy-3-[(1-ethoxyethyl)mercaptomethyl]quinuclidine benzoic acid salt To 3-hydroxy-3-[(1-ethoxyethyl)mercaptomethyl]quinuclidine (15.52 g, 63.3 mmol) was added toluene (75 mL). Benzoic acid (7.73 g, 63.3 mmol) was added in one portion. The reaction mixture was stirred for 18 hours and the white precipitate that formed was filtered and washed with toluene (3×30 mL) to give 3-hydroxy-3-[(1-ethoxyethyl)mercaptomethyl]quinuclidine benzoic acid salt (16.15 g, 44.0 mmol, 69%) as a white solid containing 10% toluene by weight.
$^1$H NMR (400 MHz, CDCl$_3$, 1:1 mixture of diastereomers) δ 8.05 (d, J=6.9 Hz, 2H), 7.42-7.35 (m, 3H), 4.70-4.60 (m 1H), 3.81-3.68 (m, 1H), 3.58-3.48 (m, 1H), 3.30-3.00 (m, 7H), 2.90-2.79 (m, 1H), 2.38-2.28 (m, 1H), 2.20-2.12 (m, 1H), 1.85-1.70 (m, 2H), 1.68-1.55 (m, 4H), 1.27-1.18 (m, 3H)

Example 9

Preparation of 3-hydroxy-3-[(1-butoxy-1-ethyl)mercaptomethyl]quinuclidine

To a solution of the epoxide of 3-methylenequinuclidine (2.80 g, 20.1 mmol) and acetyl thiobutoxyethylacetal (3.55 g, 20.1 mmol) in toluene (11 mL) was added methanol (15 mL) and the reaction mixture was cooled to 0-5° C. Potassium tert-butoxide (0.23 g, 2.01 mmol) was then added and the reaction was maintained at 0-5° C. for 30 minutes before warming to room temperature for an additional 1 hour. The reaction mixture was then transferred to a separatory funnel and charged with water (20 mL) and 50% sodium hydroxide solution (3 mL) and toluene (25 mL). The phases were separated and the aqueous phase was extracted with toluene (2×25 mL). The organic extracts were combined and washed with saturated sodium chloride solution (30 mL) and concentrated under reduced pressure to provide a viscous yellow oil constituted of 7:93 by weight of toluene and 3-hydroxy-3-[(1-butoxy-1-ethyl)mercaptomethyl]quinuclidine (4.86 g, 16.6 mmol, 83%, as a 1:1 mixture of diastereomers) respectively. The product was used directly without further purification.
$^1$H NMR (400 MHz, CDCl$_3$, 1:1 mixture of diastereomers) δ 5.71 (q, J=6.3 Hz, 0.5H), 4.63 (q, J=6.5 Hz, 0.5H), 3.79-3.72 (m, 0.5H), 3.67-3.60 (m, 0.5H), 3.49-3.42 (m, 1H), 3.40-3.37 (m, 1H), 3.10-2.72 (m, 7.5H), 2.70-2.62 (m, 1.5H), 2.11-2.01 (m, 1H), 1.98-1.89 (m, 1H), 1.79 (s, 0.5H), 1.62-1.50 (m, 7.5H), 1.42-1.29 (m, 3H), 0.95-0.89 (m, 3.0)

Example 10

Preparation of 2-methylspiro(1,3-oxathiolane-5,3') quinuclidine

To a solution of 3-hydroxy-3-[(1-ethoxyethyl)mercaptomethyl]quinuclidine (1.91 g, 7.77 mmol, 1:1 mixture of diastereomers) in toluene (1 mL) and n-butanol (12 mL) was added p-toluenesulfonic acid monohydrate (2.96 g, 15.5 mmol). The reaction mixture was then heated to 80° C. for 20 hours and then cooled to room temperature. Water (40 mL) was added to the reaction mixture and the reaction was concentrated to azeotropically remove n-butanol. The final volume was adjusted to 20 mL with water and the pH was adjusted to 11 with 50% sodium hydroxide solution. The aqueous mixture was transferred to a separatory funnel and extracted with toluene (3×30 mL). The organic fractions were combined and washed with saturated sodium chloride solution (20 mL). The toluene solution was then concentrated to give 2-methylspiro(1,3-oxathiolane-5,3') quinuclidine (1.01 g, 5.07 mmol, 65%) as a 2:1 mixture of cis:trans isomers in toluene solution (determined by $^1$H NMR).

Example 11

Preparation of 2-methylspiro(1,3-oxathiolane-5,3')-quinuclidine

A solution of 3-hydroxy-3-[(1-ethoxyethyl)mercaptomethyl]quinuclidine (14.7 g, 59.7 mmol) in toluene (147 mL) was cooled to 0-5° C. at which time trifluoroacetic acid (68.1 g, 597 mmol) was added dropwise over 15 minutes. The reaction was stirred for 2 hours at which time 10% sodium hydroxide solution (125 mL) was added and the reaction mixture was stirred for an additional 30 minutes. The aqueous phase was extracted with toluene (2×100 mL) and concentrated to yield 2-methylspiro (1,3-oxathiolane-5,3')-quinuclidine (6.7 g, 33.6 mmol, 56%, 75:25 cis:trans mixture of diastereomers) as a yellow oil.
$^1$H NMR (400 MHz, CDCl$_3$, 75:25 mixture of diastereomers) δ 5.24 (q, J=5.8 Hz, 0.25H), 5.11 (q, J=5.8 Hz, 0.75H), 3.23 (d, J=8.9 Hz, 0.75H), 3.09-2.98 (m, 1H), 2.91-2.70 (m, 6H), 2.15-2.10 (m, 0.75H), 2.09-1.98 (m, 0.5H), 1.94-1.90 (m, 0.25H), 1.88-1.80 (m, 0.75H), 1.68-1.51 (m, 5H), 1.49-1.31 (m, 1H)

Example 12

Preparation of 2-methylspiro(1,3-oxathiolane-5,3')-quinuclidine 3-hydroxy-3-[(1-ethoxyethyl)mercaptomethyl]quinuclidine benzoic acid salt (2.0 g, 5.44 mmol) was suspended in toluene (20 mL) and cooled to 0-5° C. Trifluoroacetic acid (6.21 g, 54.4 mmol) was added dropwise and the reaction mixture was stirred for 18 hours then concentrated to dryness. To the crude material was added toluene (30 mL) and 10% sodium hydroxide (20 mL). The aqueous layer was extracted with toluene (2×30 mL) and the combined organic layers were washed with water (20 mL). The organic layer was concentrated to yield 2-methylspiro(1,3-oxathiolane-5,3')-quinuclidine (0.861 g, 4.31 mmol, 79%) as a colourless oil as a 75:25 mixture of diastereomers.

Example 13

Preparation of 2-methylspiro(1,3-oxathiolane-5,3') quinuclidine p-toluenesulfonic acid salt To a solution of 3-hydroxy-3-[(1-ethoxyethyl)mercaptomethyl]quinuclidine (1.58 g, 6.46 mmol) in toluene (1 mL) and 2-propanol (10 mL) was added p-toluenesulfonic acid monohydrate (2.46 g, 12.9 mmol). The reaction mixture was then heated to 80° C. for 14 hours and then cooled to room temperature. The reaction mixture provided 2-methylspiro(1,3- oxathiolane-5,3') quinuclidine p-toluenesulfonic acid salt (1.18 g, 3.18 mmol, 49%) as a 3:1 mixture of cis:trans isomers in solution.

Example 14

Preparation of 2-methylspiro(1,3-oxathiolane-5,3') quinuclidine trifluoroacetic acid salt A solution of 3-hydroxy-3-[(1-butoxy-1-ethyl)mercaptomethyl]quinuclidine (3.07 g, 11.2 mmol) in toluene (36 mL) was cooled to 0-5° C. Trifluoroacetic acid (12.77 g, 112 mmol) was then slowly added over 10 minutes. The reaction was maintained at 0-5° C. for an additional 40 minutes before warming to room temperature for 20 hours to give a solution of 2-methylspiro(1,3-oxathiolane-5,3') quinuclidine trifluoroacetic acid salt (3.00 g, 9.57 mmol, 85%) as a 3:1 mixture of cis:trans isomers as determined by $^1$H NMR.

Example 15

Preparation of 2-methylspiro(1,3-oxathiolane-5,3') quinuclidine trifluoroacetic acid salt To a solution of the epoxide of 3-methylenequinuclidine (2.81 g, 20.2 mmol) and acetyl thioethoxyethylacetal (3.03 g, 20.4 mmol) in toluene (20 mL) was added methanol (15 mL) and the reaction mixture was cooled to 0-5° C. Potassium tert-butoxide (0.23 g, 2.02 mmol) was then added and the reaction was maintained at 0-5° C. for 15 minutes before warming to room temperature for an additional 2 hours. The reaction mixture was then concentrated under reduced pressure. Toluene (9 mL) was added and the reaction was again concentrated under reduced pressure. Toluene (30 mL) was then added and the reaction was cooled to 0-5° C. and trifluoroacetic acid (23.03 g, 20.2 mmol) was slowly added over 20 minutes. The reaction was maintained at 0-5° C. for an additional 30 minutes before warming to room temperature for 20 hours to give a solution of 2-methylspiro(1,3-oxathiolane-5,3') quinuclidine trifluoroacetic acid salt (4.70 g, 15.0 mmol, 74%) as a 3:1 mixture of cis:trans isomers as determined by $^1$H NMR.

Example 16

Preparation of cis-2-methylspiro(1,3-oxathiolane-5,3') quinuclidine camphor-sulfonic acid salt To a solution of the epoxide of 3-methylenequinuclidine (10.79 g, 77.5 mmol) and acetyl thioethoxyethylacetal (12.06 g, 81.4 mmol) in toluene (100 mL) was added methanol (55 mL) and the reaction mixture was cooled to 0-5° C. Potassium tert-butoxide (0.87 g, 7.75 mmol) was then added and the reaction was maintained at 0-5° C. for 15 minutes before warming to room temperature for an additional 2 hours. The reaction mixture was then concentrated under reduced pressure. Toluene (110 mL) was added and the reaction was again concentrated under reduced pressure to 110 mL total volume. The reaction was cooled to 0-5° C. and trifluoroacetic acid (88.37 g, 775 mmol) was slowly added over 30 minutes. The reaction was maintained at 0-5° C. for an additional 30 minutes before warming to room temperature for 16 hours. The reaction was then cooled to 5-10° C. and slowly charged with 50% sodium hydroxide solution (62.0 g, 775 mmol). The biphasic mixture was transferred to a separatory funnel and the aqueous phase was adjusted to pH=12 by the addition of 50% sodium hydroxide solution (5 mL). The liquid phases were separated and the aqueous phase was extracted with toluene (4×33 mL), the organic extracts were combined and washed with water (1×10 mL). The organic extract was then concentrated to 105 mL, methanol (1.69 g, 52.8 mmol) and (+/−)-camphorsulfonic acid (8.83 g, 38.0 mmol) were charged to the reaction and the mixture was stirred at room temperature for 22 hours. The white precipitate which formed was collected by filtration, washed with toluene (2×11 mL) and dried under vacuum at room temperature to give 2-methylspiro(1,3-oxathiolane-5,3') quinuclidine camphorsulfonic acid salt (12.04 g, 27.9 mmol, 36%) as a 95:5 mixture of cis:trans isomers as determined by $^1$H NMR.

$^1$H NMR (400 MHz, CDCl$_3$, cis-isomer) δ 5.16 (q, J=5.9 Hz, 1H), 3.57-3.41 (m, 4H), 3.39-3.30 (m, 2H), 3.27 (d, J=11.2 Hz, 1H), 3.22 (d, J=14.4 Hz, 1H), 3.03 (d, J=11.2 Hz, 1H), 2.83 (d, J=14.4 Hz, 1H), 2.61-2.53 (m, 1H), 2.41-2.39 (M, 1H), 2.34-2.27 (m, 1H), 2.21-2.13 (m, 4H), 2.06-1.78 (m, 3H), 1.57 (d, J=5.7 Hz, 3H), 1.42-1.36 (m, 1H), 1.05 (s, 3H), 0.83 (s, 3H)

Example 17

Preparation of 2-methylspiro(1,3-oxathiolane-5,3') quinuclidine camphorsulfonic acid salt To a solution of 3-hydroxy-3-mercaptomethylquinuclidine camphorsulfonic acid salt (0.98 g, 2.42 mmol) in dichloromethane (6 mL) at 0-5° C. was added ethyl vinyl ether (0.19 g, 2.66 mmol) and the mixture was maintained at 0-5° C. for 1 hour. The reaction mixture was then warmed to room temperature for an additional 2 hours. Toluene (16 mL) was then added and the reaction was heated to 65° C. for 18 hours to give a solution of 2-methylspiro(1,3-oxathiolane-5,3') quinuclidine camphorsulfonic acid salt (0.48 g, 1.11 mmol, 46%) as an 18:7 mixture of cis:trans isomers as determined by $^1$H NMR (not further isolated).

The invention claimed is:
1. A process for the preparation of 1,3-oxathiolane derivatives of Formula I

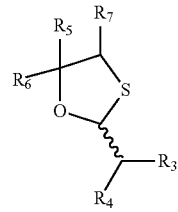

I and pharmaceutically acceptable salts thereof comprising cyclizing, in a first solvent and in the presence of a first acid, a compound of Formula VII

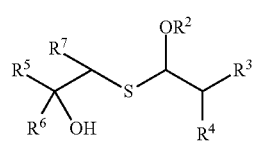

VII or a salt thereof and optionally adding an acid of a pharmaceutically acceptable salt wherein
$R^2$ is alkyl, substituted alkyl, aryl, substituted aryl, or arylalkyl;

$R^3$ and $R^4$ are independently hydrogen, alkyl, substituted alkyl, aryl, substituted aryl, or arylalkyl; and either
  (i) $R^5$, $R^6$ and $R^7$ are independently hydrogen, alkyl, substituted alkyl, aryl, substituted aryl, arylalkyl, or substituted arylalkyl provided that at least one of $R^5$ and $R^6$ is alkyl, substituted alkyl, aryl, substituted aryl, arylalkyl, or substituted arylalkyl;
  (ii) $R^5$ and $R^6$ form a ring group together with the carbon to which they are bonded and $R^7$ is hydrogen, alkyl, substituted alkyl, aryl, substituted aryl arylalkyl or substituted arylalkyl; or
  (iii) $R^5$ and $R^7$ form a ring group together with the carbons to which they are bonded and $R^6$ is hydrogen, alkyl, substituted alkyl, aryl, substituted aryl arylalkyl or substituted arylalkyl.

2. The process of claim 1, wherein the compound of Formula VII is a compound of Formula VIIa

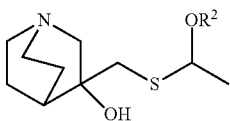

VIIa or a salt thereof, wherein $R^2$ is alkyl, substituted alkyl, aryl, substituted aryl, arylalkyl or substituted arylalkyl.

3. The process of claim 2, wherein the compound of Formula VIIa is a compound of Formula VIIaa

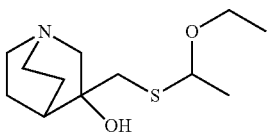

VIIaa or a salt thereof.

4. The process of claim 2, wherein the compound of Formula VIIa is a compound of Formula VIIab

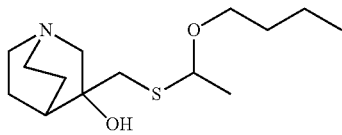

VIIab or a salt thereof.

5. The process of claim 1, wherein the first acid is an organic sulfonic acid, trifluoroacetic acid, a phosphorous oxyacid, sulfuric acid or a Lewis acid.

6. The process of claim 4, wherein the first acid is an organic sulfonic acid or trifluoroacetic acid.

7. The process of claim 1, wherein the first solvent is an aromatic hydrocarbon or an alcohol.

8. The process of claim 1 wherein the compound of Formula VII is prepared by reacting, in the presence of a first base, a compound of Formula VI:

VI with a compound of Formula IV

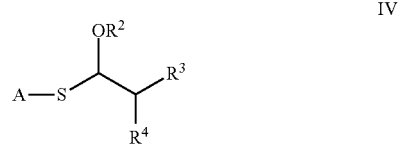

IV or a salt thereof, wherein
  A is hydrogen or $COR^1$;
  $R^1$ and $R^2$ are independently alkyl, substituted alkyl, aryl, substituted aryl, or arylalkyl;
  $R^3$ and $R^4$ are independently hydrogen, alkyl, substituted alkyl, aryl, substituted aryl, or arylalkyl; and either
    (i) $R^5$, $R^6$ and $R^7$ are independently hydrogen, alkyl, substituted alkyl, aryl, substituted aryl, arylalkyl, or substituted arylalkyl provided that at least one of $R^5$ and $R^6$ is alkyl, substituted alkyl, aryl, substituted aryl, arylalkyl, or substituted arylalkyl;
    (ii) $R^5$ and $R^6$ form a ring group together with the carbon to which they are bonded and $R^7$ is hydrogen, alkyl, substituted alkyl, aryl, substituted aryl arylalkyl or substituted arylalkyl; or
    (iii) $R^5$ and $R^7$ form a ring group together with the carbons to which they are bonded and $R^6$ is hydrogen, alkyl, substituted alkyl, aryl, substituted aryl arylalkyl or substituted arylalkyl.

9. The process of claim 8 wherein the compound of Formula VII is not isolated.

* * * * *